(12) United States Patent
Casutt et al.

(10) Patent No.: US 8,257,362 B2
(45) Date of Patent: *Sep. 4, 2012

(54) DISTANCE MEASURING INSTRUMENT FOR PEDICLE SCREWS

(75) Inventors: Simon Casutt, Gossau (CH); Nimrod Meier, Schaffhausen (CH); Marc Huber, Turbenthal (CH)

(73) Assignee: Zimmer GmbH, Winterthur (CH)

( * ) Notice: Subject to any disclaimer, the term of this patent is extended or adjusted under 35 U.S.C. 154(b) by 1344 days.

This patent is subject to a terminal disclaimer.

(21) Appl. No.: 11/866,197

(22) Filed: Oct. 2, 2007

(65) Prior Publication Data

US 2008/0039841 A1 Feb. 14, 2008

Related U.S. Application Data

(63) Continuation of application No. 10/830,504, filed on Apr. 23, 2004, now Pat. No. 7,275,336.

(30) Foreign Application Priority Data

Apr. 24, 2003 (EP) .................................. 03009327

(51) Int. Cl.
*A61B 17/60* (2006.01)
(52) U.S. Cl. ..................................... 606/102
(58) Field of Classification Search .............. 33/747, 33/787, 797, 798, 800, 801; 606/102
See application file for complete search history.

(56) References Cited

U.S. PATENT DOCUMENTS

| 1,990,138 | A | | 2/1935 | Schuster |
| 3,750,652 | A | * | 8/1973 | Sherwin .......................... 606/90 |
| 3,815,247 | A | | 6/1974 | Debrunner |
| 4,899,761 | A | * | 2/1990 | Brown et al. ................. 600/594 |
| 4,972,602 | A | | 11/1990 | Howes |
| 5,070,623 | A | | 12/1991 | Barnes |
| 5,188,121 | A | | 2/1993 | Hanson |
| 5,329,933 | A | | 7/1994 | Graf |
| 5,428,903 | A | | 7/1995 | Pocci |
| 5,454,175 | A | | 10/1995 | Li |
| 2004/0116835 | A1 | * | 6/2004 | Holmes ......................... 600/594 |

OTHER PUBLICATIONS

European Search Report dated Sep. 23, 2003 re: EPO Appl. 03 009 327.2; Translation of European Search Report dated Sep. 23, 2003 re: EPO Appl. 03 009 327.2.

* cited by examiner

*Primary Examiner* — Thomas C. Barrett
*Assistant Examiner* — Michael Araj
(74) *Attorney, Agent, or Firm* — Seager Tufte & Wickhem LLC

(57) ABSTRACT

The invention relates to a distance measuring instrument for pedicle screws which detects the spacing between two pedicle screws (3, 3') with the ends (26, 27) of two crossing limbs (11, 12) and displays it on a crossbar (25) fixedly connected to one of the limbs at a scale (22). Since the second limb (12) is divided into a pointer (16*a*) and into a flexural spring extending parallel to it at which a pronounced thumb grip (21*a*) is fastened, and since the thumb grip is connected to a scale (24) via which a pre-determined pre-tension can be read off relative to the pointer (16*a*), a spacing measurement can take place under a controlled pre-tension.

17 Claims, 4 Drawing Sheets

Figure 3:
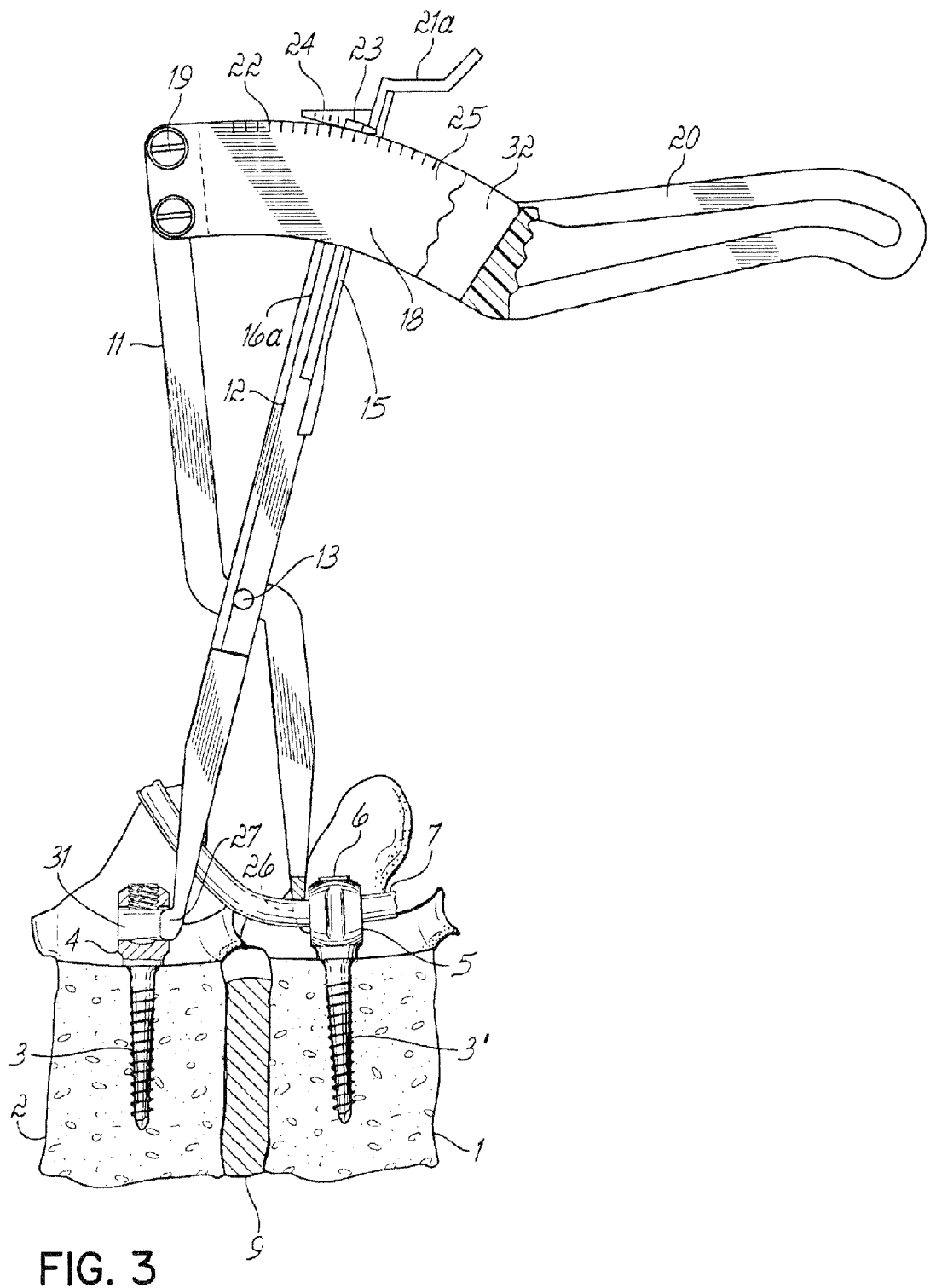

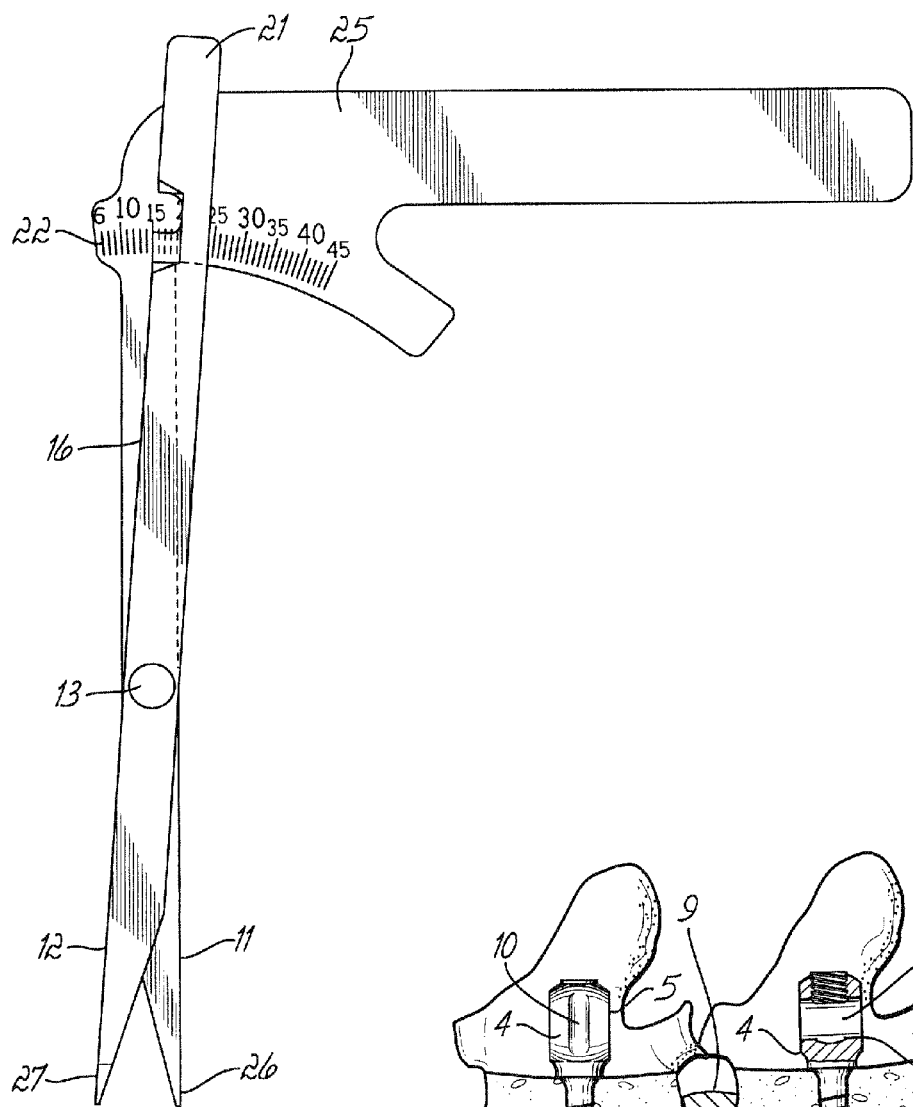
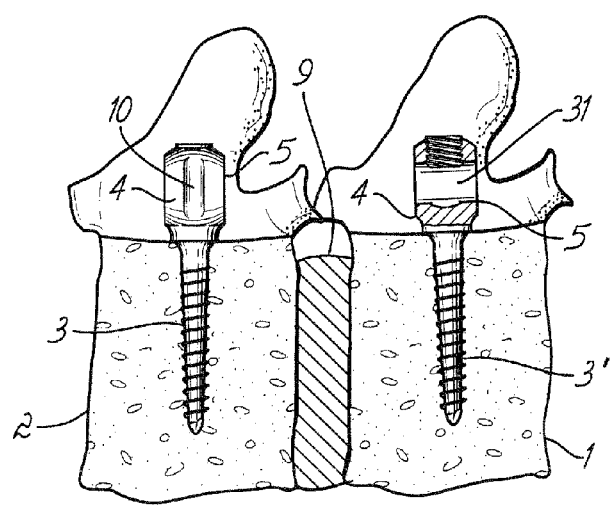
PRIOR ART
FIG. 2
FIG. 1

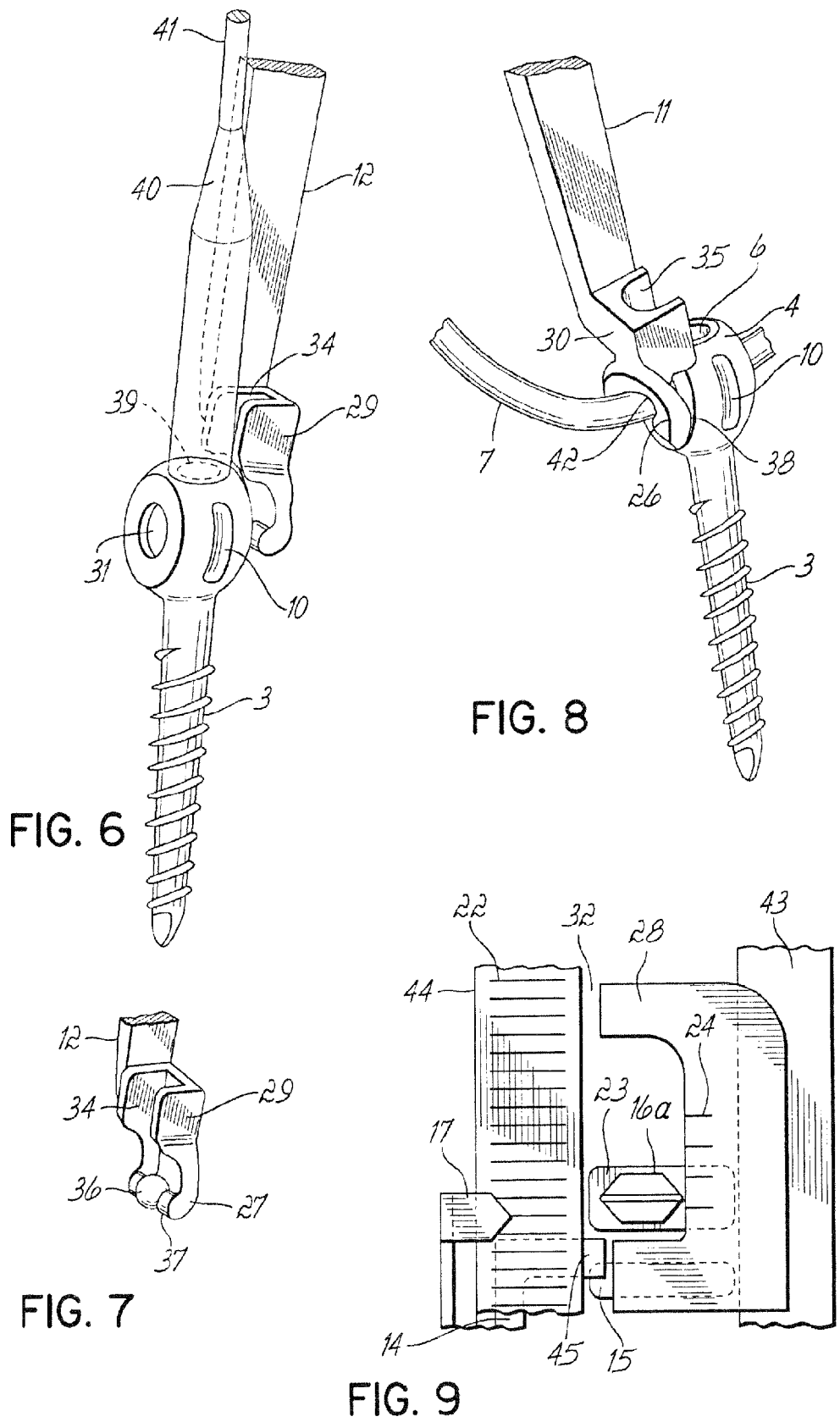

DISTANCE MEASURING INSTRUMENT FOR PEDICLE SCREWS

The invention relates to a distance measuring instrument for pedicle screws having two limbs which cross at an axis of rotation and whose ends can be positioned at two pedicle screws screwed into adjacent spinal vertebrae, with a first limb merging at the opposite side to its end into a crossbar which is provided with an arc-shaped scale part, with the second limb having a projection projecting over the crossbar for adjustment and being formed as a pointer to indicate the spacing between the pedicle screws with the pointer at a scale of the scale part. Such a spacing measurement serves for the defining of the length of components which are intended to bridge the distance between the two pedicle screws.

The company Centerpulse Orthopedics Ltd. (Altgasse 44, CH-6340 Baar) has a spacing measurement device in its instruments such as is shown in FIG. 2 as prior art. Such a measurement device allows the spacing between two screwed in pedicle screws to be measured when the screw heads are easily visible and the contact of the ends can thus be visually inspected. When the heads of the pedicle screws are not directly visible, a spacing measurement is very difficult.

It is the object of the present invention to improve this condition with respect to operating techniques which only provide for a small, minimum invasive operation field. This object is satisfied by the characterising part of claim 1 in that the second limb is divided into a pointer and a flexural spring extending parallel to it, at which a pronounced thumb grip is fastened; and in that the crossbar is shaped as a handle to produce a spreading force at the ends via the flexural spring which can be read off relative to the pointer via a scale connected to the thumb grip.

This arrangement has the advantage that a tactile feedback for the contacting of the ends is present at the thumb grip during the reading of the spacing of the ends under pre-tension. It has furthermore been found that an initial yielding between two vertebrae can also be taken into account by a pre-determined pre-tension force on spreading to determine the installation length of a supporting element.

Advantageous further developments of the invention are shown by the features of dependent claims 2 to 10.

A robust and less susceptible design for the spacing measurement device results when the second limb with pointer and flexural spring is guided at both sides in an elongate slot of the crossbar. In the arc-shaped scale part, a likewise arc-shaped groove for a key is worked in which is designed as a trailing pointer and is carried along by the pointer at the second limb at a projecting dog. The pointer actually connected to the key remains at the scale of the arc-shaped scale part as a stored value, irrespective of whether the pointer of the second limb has to reduce its spacing, for example in order to move centring elements out of centring bores at the pedicle screws.

The tactile feedback with respect to the spacing position reached between two pedicle screws can be substantially improved if matching centring devices are attached to the ends of the limbs which centre in the spreading direction at the head of a pedicle screw or at elements connected thereto. The end of a limb can thus be formed in the spreading direction with a nose in the form of a projecting hemisphere or of a cone stub in order to be centred in a bore of the head. As long as such a limb is under pre-tension in the spreading direction, the centring elements cannot slide off. At the same time, by a light shaking at the limb, the tactile feedback is given that the end is centred at its provided position. A centring can also be carried out at the emerging of the band or cable with a limb end which is fork-shaped even with pedicle screws where a cable has already been drawn in the head.

It is furthermore advantageous to crank the ends of the two limbs in the form of laterally offset projections such that the limbs themselves and the rest of the distance measuring instrument lie laterally offset relative to the plane set up by the two pedicle screws. This allows tools and centring elements to be used such as are described in a parallel application in an independent manner because they are arranged spatially offset. If instruments or centring parts are used which engage perpendicularly from above at the head of a pedicle screw which is hardly visible, then the ends of the limbs can additionally have a guiding fork in the spreading direction with which the ends are guided on their way to the head until an actual centring at the head is possible.

Further advantages in handling arise when the scale for the reading of the pre-tension is attached to a hook which engages behind the pointer with clearance to prevent over-stressing of the flexural spring and to read off the pre-tension within this clearance. If the limbs of the measuring device are made of metal (e.g. of a non-rusting steel alloy) and if the crossbar, which guides the second limb, is made of plastic, a low inherent weight and a favourable and silent material pairing for the guide results. It is furthermore possible to provide a whole set of different ends pushable onto the limbs as adapter pieces which have a fork shape in the direction of the limb axis, a centring sphere or cone shape in the spreading direction, a lateral offset and/or a fork shape in the spreading direction.

Figure 4:
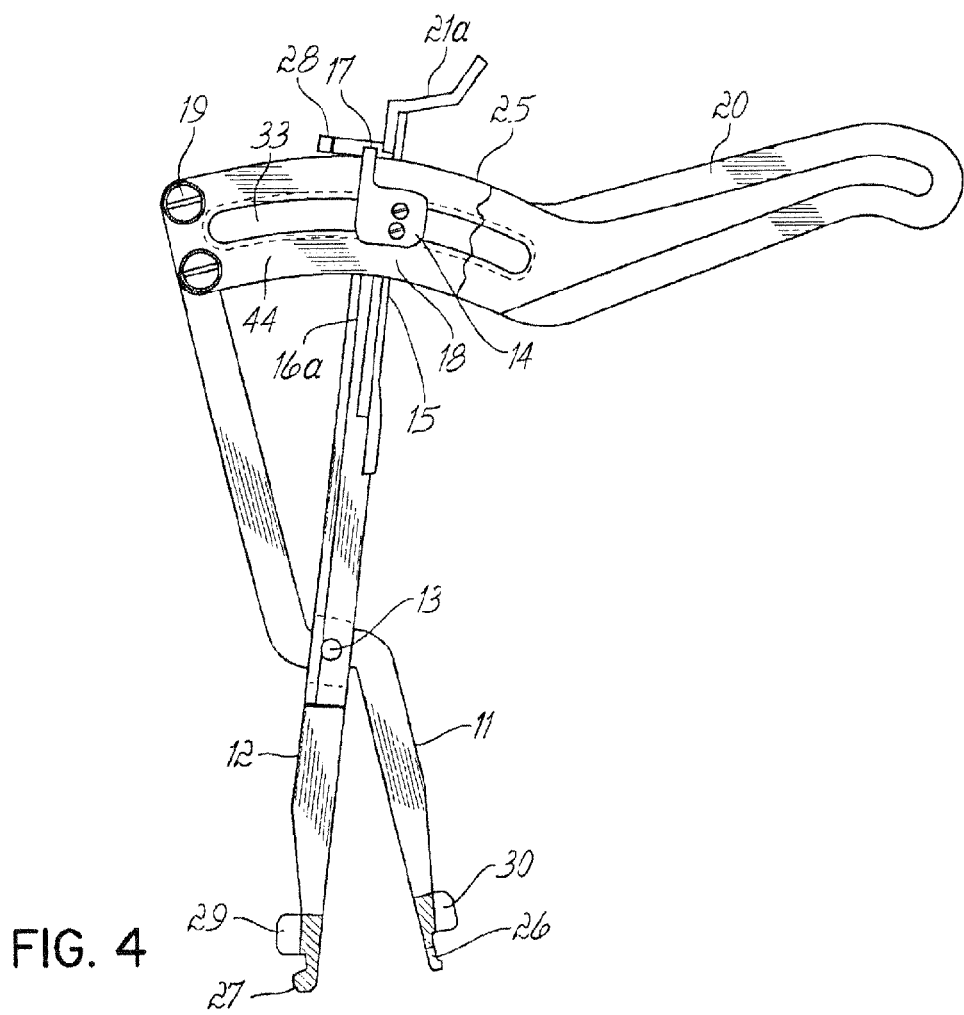
Figure 5:
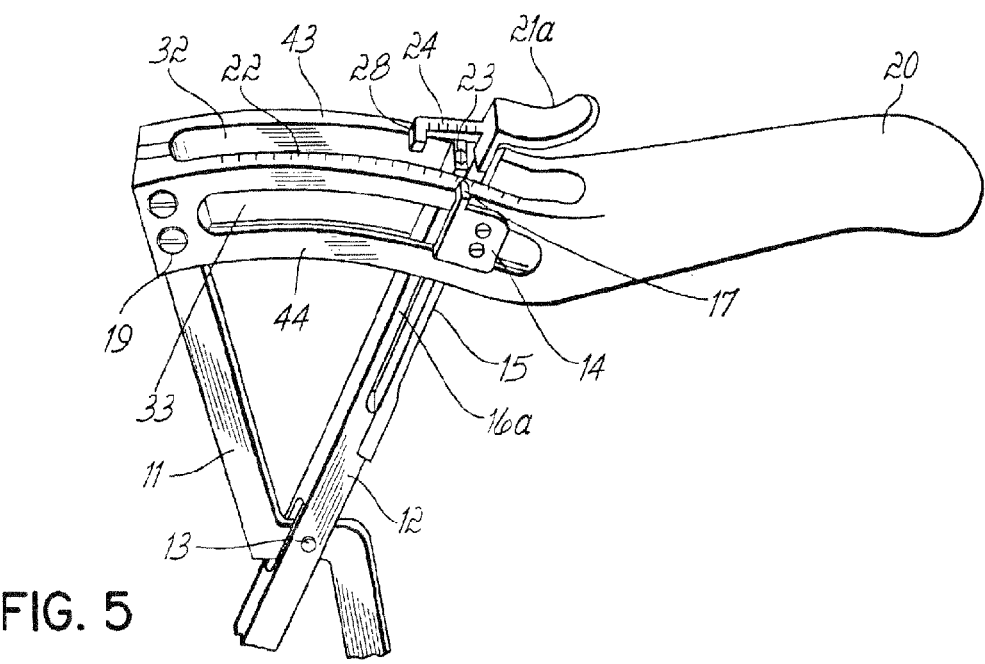

The invention will be described with reference to embodiments in the following. There are shown:

FIG. 1: schematically, a section with two pedicle screws screwed into adjacent vertebrae;

FIG. 2: schematically, a view of a known spacing measurement device for the pedicle screws of FIG. 1;

FIG. 3: schematically, a side view of a distance measuring instrument in accordance with the invention;

FIG. 4: schematically, a side view of a further distance measuring instrument analogue to FIG. 3;

FIG. 5: schematically, a view obliquely from above of the distance measuring instrument of FIG. 4;

FIG. 6: schematically, a section at the end of a second limb which contacts at its offset end a pedicle screw with a screwed in centring part;

FIG. 7: schematically, an end of the second limb of FIG. 6 with a hemispherical projection for the centring at a passage bore of the pedicle screw;

FIG. 8: schematically, a section at the end of a first limb which at its offset end, which is centred as a fork at a cable drawn through the pedicle screw, contacts the head of the pedicle screw; and FIG. 9: schematically, a very enlarged section of the scale part and the displays of the distance measuring instrument of FIG. 4.

FIGS. 1 and 2 show how a spacing measurement has previously been made between two pedicle screws. Two pedicle screws 3, 3' are screwed into two adjacent spinal vertebrae 1, 2 which are separated by an intervertebral disc 9. Each of the pedicle screws 3, 3' has a head 4, with end faces 5, at which bridging parts are later pushed. The heads 4 are aligned such that their passage bores 31 are flush. There are notches 10 at the side at the heads 4 at which further instruments can be aligned. A previously known distance measuring instrument consists of two limbs 11, 12 which cross at an axis of rotation 13 and whose ends 26, 27 can be spread, for example to detect the spacing between the two pedicle screws 3, 3' and to read it off with the second limb 12 as the pointer 16 at an arc-shaped scale 22 which is attached to a crossbar 25 of the first limb 11. The pointer 16 is moved with a projection 21 for this purpose.

A first example of the invention is shown in FIG. 3. A distance measuring instrument contacts two adjacent vertebrae 1, 2 with pedicle screws 3, 3' at its limbs 11, 12. The first limb 11 has a fork-shaped end 26 with which it contacts the pedicle screw 3' and with which it is simultaneously centred at a cable 7 projecting from the head of the pedicle screw. The cable 7 is fixed in a passage bore 31 by a clamping screw 6. The fork-shaped end 26 contacts the head of the pedicle screw 3' at a slight pre-tension. The second pedicle screw 3 likewise has a passage bore 31 in its head 4 into which the cable 7 is drawn at a later time. The second limb 12 is centred at this passage bore 31 at its end 27 which has a projection projecting in the spreading direction.

The two limbs 11, 12 cross at an axis of rotation 13. A cross bar 25 made of plastic is screwed to the first limb 11 opposite to its end 26 and first projects laterally as a scale part 18 with a curvature in the form of an arc of a circle with the axis of rotation 13 as the centre point and merges into a handle 20. The two limbs 11, 12 are made of metal, for example of a non-rust steel. The first limb is fastened to the crossbar 25 by screws 19. The second limb 12 is guided in an elongate slot 32 of the crossbar 25 and split in its longitudinal direction into two components, a pointer 16a and a flexural spring 15 which are both captured in the elongate slot 32. The flexural spring 15 extends parallel to the pointer 16a, is fastened to the second limb 12 by screws (not shown), for example, and is fixedly connected at its upper end to a thumb grip 21a projecting above the crossbar 25. The pointer 16a has at its upper end an arrow marking 23 which indicates the spacing of the two ends 26, 27 on a scale 22 of the arc-shaped scale part 18. When the handle 20 is gripped by the hand and the flexural spring 15 is drawn towards the hand by the thumb grip 21a, a pre-tension arises at the ends 26, 27 of the limbs 11, 12 which corresponds in a tactile manner to a feedback on the contacting of the ends 26, 27 at the pedicle screws 3, 3', with the spacing of the ends being able to be read off at a pre-determined pre-tension because a scale 24 has been attached to the thumb grip 21a at which the pre-tension can be read off relative to the arrow marking 23 of the pointer 16a. An advantage of the device consists of the fact that it can be operated with one hand and leaves the second hand free for the surgeon for additional manipulations such as the holding back of tissue parts standing in the way.

A further embodiment is shown in FIGS. 4 to 9 in which further improvements to the embodiment of FIG. 3 are included. The same reference numerals have been used as in FIG. 3. The elongate slot 32 (FIGS. 5 and 9) divides the curved scale part 18 of the crossbar 25 into a front part 44 and into a rear part 43. A continuous, curved groove 33 has been applied in the front part 44 and a key 14, which itself has a friction brake, is displaceably supported in this in order to be taken along in the spreading direction as a trailing pointer 17 by the pointer 16a. For this purpose (FIG. 9), a dog 45 is attached to the key 14 which projects into the elongate slot 32 and is taken along by the pointer 16a. The actual key 14 is, for example, inserted from the side of the elongate slot 32 and secured from the front by a trailing pointer 17 screwed on as a securing plate. On the drawing of the thumb grip 21a, the trailing thermometer 17 is taken along by the pointer 16a. If the ends 26, 27 now meet the resistance of the pedicle screws, the flexural spring can be pre-tensioned so much via the thumb grip until a pre-determined tension has been reached. At this tension, the largest spacing also occurs between the two pedicle screws 3, 3'. On the subsequent relief of the thumb grip, the trailing pointer remains at the position of the largest spacing and thus stores the measured value without any influencing taking place on the further moving together of the tips 26, 27, for example for the releasing of centring projections 36 from the passage bores 31 of pedicle screws.

The scale 24 for the reading of the pre-tension is attached to a hook 28 bent out of the thumb grip 21a which is partly guided around the pointer 16a in order to avoid over-straining of the flexural spring 15 in that the hook 28 abuts the pointer 16a. This means that the pointer 16a must be so stable that it is also not plastically deformed on non-professional handling of the thumb grip 21a. In FIGS. 6, 7 and 8, alternatives are shown in the region of the ends 26, 27 of the limbs 11, 12. Both limbs 11 and 12 are cranked toward the end and have projections 29, 30 offset laterally relative to the spreading direction which each form the end. The lateral offset has the advantage that the whole distance measuring instrument is arranged laterally offset relative to the pedicle screws and does not take up the space directly above the pedicle screws for itself. Furthermore, the projections 29, 30 have opened guiding forks 34, 35 in the spreading direction with which they can be guided from the outside up to the head of the pedicle screw at a slight pre-tension along centring parts 39 or along tubular tools which sit at the head of the pedicle screw. Such a centring part 39 is shown with its under end in FIG. 6. It has been screwed into the thread provided for a clamping screw 6 and tapers from a cylindrical start via a cone 40 up to a flexurally elastic central part 41. The cable 7 is already fixed by a clamping screw 6 in FIG. 8. A tubular mating holder having an internally guided screwdriver which is described in a parallel application can be used for the fixing. Such a mating holder is supported in a shape matched manner in notches 10 of the head 4 and is continued upwardly in tubular shape. If this mating holder is left in position after the screwing in of the clamping screw 6, it can be used like the centring part 39 for the guiding of a lateral projection 30 with a guiding fork 35 on its way to the pedicle screw. The end 26 is made to form a fork 42 which is centred at the drawn in cable 7. The pre-tension to the pedicle screw is applied via pressure zones 38 which are arranged at both sides of the cable 7 at the fork 42.

A hemispherical projection 36 is shown for the lateral projection 29 in FIG. 7 and can be centred in the passage bore 31 of a pedicle screw. Pressure zones 37, which can transfer a pre-tension force to the pedicle screw 3, are arranged at both sides of the hemispherical projection 36.

PARTS LIST 1 spinal vertebra
2 spinal vertebra
3 pedicle screw
3' pedicle screw
4 head
5 end face
6 clamping screw
7 cable
8
9 intervertebral disc
10 notch
11 limb
12 limb
13 axis of rotation
14 key
15 flexural spring
16 pointer
16a pointer 17 trailing pointer
18 scale part
19 screw
20 handle
21 projection
21a thumb grip
22 scale (spacing)
23 arrow marking
24 scale (pre-tension)
25 crossbar
26 end
27 end
28 hook
29 lateral projection
30 lateral projection
31 passage bore
32 elongate slot
33 groove
34 guide fork
35 guide fork
36 hemispherical projection
37 pressure zone
38 pressure zone
39 centring part
40 cone
41 flexurally elastic part
42 fork
43 rear part
44 front part
45 dog

The invention claimed is:

1. A distance measuring instrument for pedicle screws, comprising first and second limbs which cross at an axis of rotation and whose ends can be positioned at two pedicle screws screwed into adjacent spinal vertebrae, with the first limb including a scale part at its opposite end, the scale part being formed as a first pointer to display a spacing between two pedicle screws with the first pointer at a first scale of the scale part, wherein the second limb includes a second pointer and a spring and wherein the scale part is incorporated into a handle configured to produce a spreading force at the ends via the spring, the spreading force being readable relative to the second pointer via a second scale.

2. A distance measuring instrument in accordance with claim 1, wherein the scale part includes an arc-shaped crossbar of the first limb.

3. A distance measuring instrument in accordance with claim 1, wherein the spring is a flexural spring.

4. A distance measuring instrument in accordance with claim 1, wherein the first limb includes an elongate slot, the second limb being guided relative to the first limb in the elongate slot.

5. A distance measuring instrument in accordance with claim 1, wherein the scale part includes a groove and the second pointer includes a key defining a trailing pointer guided along the groove, the trailing pointer showing the spacing of the ends of the first and second limbs on the first scale, the key remaining in place at a maximum spacing measured.

6. A distance measuring instrument in accordance with claim 1, wherein at least one of the ends of the first and second limbs is designed as a fork configured to be centered at a band or cable drawn through a head of a pedicle screw.

7. A distance measuring instrument in accordance with claim 1, wherein at least one of the ends of the first and second limbs includes a hemispherical projection configured to be centered at a passage bore in a head of a pedicle screw.

8. A distance measuring instrument in accordance with claim 1, wherein the first and second limbs define respective first and second axes, the first and second limbs including respective first and second projections respectively laterally offset relative to the first and second axes.

9. A distance measuring instrument in accordance with claim 8, wherein the projections define adapter pieces pushable onto the limbs.

10. A distance measuring instrument in accordance with claim 8, wherein each of the projections includes a guide fork oriented in a spreading direction, the projections configured to guide the respective ends of the first and second limbs to a head of a pedicle screw along a centering part thereof screwed into the head of the pedicle screw.

11. A distance measuring instrument in accordance with claim 1, wherein the second limb includes a thumb grip, the second scale being configured for reading of pretension and being attached to a hook that engages behind the second pointer to prevent overstraining of the spring by the thumb grip.

12. A distance measuring instrument in accordance with claim 1, wherein the first limb includes a crossbar having a plastic, the first and second limbs including a metal.

13. A method of measuring a distance between pedicle screws, comprising:
   providing a distance and force measuring instrument, the distance and force measuring instrument comprising:
   first and second limbs which cross at an axis of rotation, with the first limb including a scale part, the scale part being formed as a first pointer to display a spacing with the first pointer at a first scale of the scale part, wherein the second limb includes a second pointer and a spring; and wherein the scale part is incorporated into a handle configured to produce a spreading force via the spring, the spreading force being readable relative to the second pointer via a second scale;
   coupling ends of the instrument to at least two pedicle screws;
   applying a spreading force to the pedicle screws via the spring of the handle;
   reading the spreading force indicated by the second pointer on the second scale; and
   reading the spacing indicated by the first pointer on the first scale.

14. A method in accordance with claim 13, further comprising:
   selecting an implant based on the spacing indicated by the first pointer on the first scale.

15. A method in accordance with claim 14, wherein the implant includes at least one of a cable and an element for bridging the distance between the pedicle screws.

16. An intervertebral implantation system comprising:
   first and second pedicle screws configured for implantation into adjacent vertebrae;
   a bridging element configured for coupling to the first and second pedicle screws; and
   an instrument for measuring a distance between the first and second pedicle screws, the instrument including first and second limbs which cross at an axis of rotation and whose ends can be positioned at the first and second pedicle screws screwed into the adjacent vertebrae, with the first limb including a scale part at its opposite end, the scale part being formed as a first pointer to display a spacing between the pedicle screws with the first pointer at a first scale of the scale part, wherein the second limb includes a second pointer and a spring and wherein the scale part is incorporated into a handle configured to produce a spreading force at the ends via the spring, the spreading force being readable relative to the second pointer via a second scale.

17. A system in accordance with claim 16, wherein the bridging element is flexible.

* * * * *